(12) United States Patent
Frank (10) Patent No.: US 10,390,821 B2
(45) Date of Patent: Aug. 27, 2019

(54) SOFT TISSUE FIXATION USING A LOOPED SUTURE CONSTRUCT

(71) Applicant: Joshua B. Frank, Norwalk, CT (US)

(72) Inventor: Joshua B. Frank, Norwalk, CT (US)

(*) Notice: Subject to any disclaimer, the term of this patent is extended or adjusted under 35 U.S.C. 154(b) by 1194 days.

(21) Appl. No.: 14/449,060

(22) Filed: Jul. 31, 2014

(65) Prior Publication Data
US 2014/0343604 A1 Nov. 20, 2014

Related U.S. Application Data (62) Division of application No. 13/071,771, filed on Mar. 25, 2011.

(60) Provisional application No. 61/318,344, filed on Mar. 28, 2010.

(51) Int. Cl.
| | | |
|---|---|---|
| A61F 2/08 | (2006.01) | |
| A61B 17/04 | (2006.01) | |
| A61B 17/06 | (2006.01) | |

(52) U.S. Cl.
CPC .... *A61B 17/06166* (2013.01); *A61B 17/0401* (2013.01); *A61B 2017/0464* (2013.01); *A61F 2002/0847* (2013.01)

(58) Field of Classification Search
None
See application file for complete search history.

(56) References Cited

U.S. PATENT DOCUMENTS

| | | | |
|---|---|---|---|
| 4,932,962 A | 6/1990 | Yoon et al. | |
| 5,336,231 A | 8/1994 | Adair | |
| 5,534,011 A | 7/1996 | Greene, Jr. et al. | |
| 5,643,295 A | 7/1997 | Yoon | |
| 5,683,419 A | 11/1997 | Thal | |
| 5,814,069 A | 9/1998 | Schulze et al. | |

(Continued)

FOREIGN PATENT DOCUMENTS

| | | |
|---|---|---|
| WO | WO 2010/028324 | 3/2010 |
| WO | WO2011126765 | 10/2011 |

OTHER PUBLICATIONS

Laurent Lafosse, M.D., et al., A New Technique to Improve Tissue Grip: "The Lasso Loop Stitch," The Journal of Arthroscopic and Related Surgery, vol. 22, No. 11, Nov. 2006, at pp. 1246e1-1246e3.

(Continued)

*Primary Examiner* — Shaun David
(74) *Attorney, Agent, or Firm* — Byrne Poh LLP; Nina R. Horan (57) ABSTRACT

A looped suture construct is formed by looping a suture on itself and slidably connecting the suture through an anchoring structure such that a looped end and a free end of the suture are on opposite sides of the slidable connection. The anchoring structure may be bone, a suture anchor, or another structure securely attached to bone. The looped end and the free end are passed through the soft tissue to be repaired. The free end is then passed through the looped end. Tension is applied to the free end to draw the soft tissue into contact with the desired bone, whereupon the free end is secured to maintain the tension. The looped suture end remains open and positioned on one side or surface of the soft tissue. Suture anchors of the invention are pre-loaded with at least one suture having a looped end and at least one free end.

21 Claims, 10 Drawing Sheets

(56) References Cited

U.S. PATENT DOCUMENTS

| | | | |
|---|---|---|---|
| 5,891,168 A | 4/1999 | Thal |
| 6,143,017 A | 11/2000 | Thal |
| 6,156,039 A | 12/2000 | Thal |
| 6,527,795 B1 | 3/2003 | Lizardi |
| 6,652,563 B2 | 11/2003 | Dreyfuss |
| 6,991,636 B2 | 1/2006 | Rose |
| 7,081,126 B2 | 7/2006 | McDevitt |
| 7,217,279 B2 | 5/2007 | Reese |
| 7,601,165 B2 | 10/2009 | Stone |
| 7,803,173 B2 | 9/2010 | Burkhart et al. |
| 7,883,528 B2 | 2/2011 | Grafton et al. |
| 7,883,529 B2 | 2/2011 | Sinnott et al. |
| 7,959,650 B2 | 6/2011 | Kaiser |
| 7,967,841 B2 | 6/2011 | Yuan |
| 8,118,835 B2 | 2/2012 | Weisel |
| 8,137,382 B2 | 3/2012 | Denham |
| 8,202,297 B2 | 6/2012 | Burkhart |
| 8,348,975 B2 | 1/2013 | Dreyfuss |
| 8,403,947 B2 | 3/2013 | Ochiai |
| 8,545,535 B2 | 10/2013 | Hirotsuka |
| 8,613,756 B2 | 12/2013 | Lizardi |
| 8,696,704 B2 | 4/2014 | Selvitelli |
| 8,814,905 B2 | 8/2014 | Sengun |
| 8,821,542 B2 | 9/2014 | Zirps |
| 8,821,543 B2 | 9/2014 | Hernandez |
| 8,821,544 B2 | 9/2014 | Sengun |
| 2004/0093031 A1 | 5/2004 | Burkhart et al. |
| 2004/0106950 A1 | 6/2004 | Grafton et al. |
| 2006/0079904 A1 | 4/2006 | Thal |
| 2006/0106423 A1 | 5/2006 | Weisel et al. |
| 2007/0060922 A1 | 3/2007 | Dreyfuss |
| 2007/0083236 A1 | 4/2007 | Sikora et al. |
| 2007/0112352 A1 | 5/2007 | Sorensen et al. |
| 2007/0219558 A1 | 9/2007 | Deutsch |
| 2007/0255317 A1 | 11/2007 | Fanton et al. |
| 2008/0103528 A1 | 5/2008 | Zirps et al. |
| 2008/0195205 A1 | 8/2008 | Schwartz |
| 2008/0281357 A1 | 11/2008 | Sung |
| 2009/0036905 A1 | 2/2009 | Schmieding |
| 2009/0062851 A1 | 3/2009 | Rosenblatt |
| 2009/0082805 A1 | 3/2009 | Kaiser et al. |
| 2009/0138042 A1 | 5/2009 | Thal |
| 2009/0171400 A1 | 7/2009 | van der Burg et al. |
| 2009/0248070 A1 | 10/2009 | Kosa |
| 2009/0312776 A1 | 12/2009 | Kaiser et al. |
| 2009/0318958 A1 | 12/2009 | Ochiai |
| 2010/0016892 A1 | 1/2010 | Kaiser et al. |
| 2010/0063540 A1 | 3/2010 | Maiorino |
| 2010/0292732 A1* | 11/2010 | Hirotsuka ......... A61B 17/0401 606/232 |
| 2010/0298871 A1 | 11/2010 | Ruff |
| 2011/0077667 A1 | 3/2011 | Singhatat |
| 2011/0152927 A1 | 6/2011 | Deng |
| 2011/0190815 A1 | 8/2011 | Saliman |
| 2011/0238111 A1 | 9/2011 | Frank |
| 2011/0264140 A1 | 10/2011 | Lizardi et al. |
| 2012/0130424 A1 | 5/2012 | Sengun |
| 2012/0179199 A1 | 7/2012 | Hernandez |
| 2012/0265219 A1 | 10/2012 | Rushdy |
| 2013/0046340 A1 | 2/2013 | Huxel |
| 2013/0345750 A1 | 12/2013 | Sullivan |
| 2014/0276987 A1 | 9/2014 | Saliman |
| 2014/0343606 A1 | 11/2014 | Hernandez |

OTHER PUBLICATIONS

Bruno Toussaint, M.D., et al., a New Approach to Improving the Tissue Grip of the Medial-Row Repair in the Suture-Bridge Technique: The "Modified Lasso-Loop Stitch," The Journal of Arthroscopic and Related Surgery, vol. 25, No. 6, Jun. 2009, at pp. 691 695.
Joshua S. Dines, M.D., et al., Single-row Versus Double-row Rotator Cuff Repair: Techniques and Outcomes, Journal of the American Academy of Orthopaedic Surgeons, vol. 18, No. 2, Feb. 2010, at pp. 83 93.
Brent A. Ponce, M.D., et al., Biomechanical Evaluation of 3 Arthroscopic Self-Cinching Stitches for Shoulder Arthroscopy: The Lasso-Loop, Lasso-Mattress, and Double-Cinch Stitches, The American Journal of Sports Medicine, vol. 39, No. 1, originally published online Nov. 12, 2010, at pp. 188 194.
International Search Report issued in PCT/US2011/029935, dated Jun. 10, 2011.
Written Opinion of the International Search Authority issued in PCT/US2011/029935, dated Jun. 10, 2011.
International Preliminary Report on Patentability issued in PCT/US2011/029935, dated Oct. 2, 2012.
Office Action dated Mar. 6, 2014 in U.S. Appl. No. 13/071,771.
Office Action dated Mar. 13, 2015 in U.S. Appl. No. 13/071,771.
Office Action dated Mar. 24, 2016 in U.S. Appl. No. 13/071,771.
Office Action dated Apr. 8, 2013 in U.S. Appl. No. 13/071,771.
Office Action dated May 19, 2017 in U.S. Appl. No. 13/071,771.
Office Action dated Sep. 10, 2015 in U.S. Appl. No. 13/071,771.
Office Action dated Nov. 2, 2016 in U.S. Appl. No. 13/071,771.
Office Action dated Nov. 8, 2013 in U.S. Appl. No. 13/071,771.
Office Action dated Dec. 21, 2017 in U.S. Appl. No. 13/071,771.

* cited by examiner

SOFT TISSUE FIXATION USING A LOOPED SUTURE CONSTRUCT

CROSS REFERENCE TO RELATED APPLICATION

This application is a divisional application of U.S. patent application Ser. No. 13/071,771, filed Mar. 25, 2011, now pending, which claims the benefit of U.S. Provisional Application No. 61/318,344, filed Mar. 28, 2010, the entire disclosure of each of which is incorporated by reference herein.

FIELD OF THE INVENTION

The invention relates to surgical fixation of soft tissue. More particularly, the invention relates to methods and apparatus for soft tissue repair using a looped suture construct.

BACKGROUND OF THE INVENTION

Soft tissues, such as, for example, tendons, ligaments, muscles, and the like, are attached to bone throughout the human body. Various injuries and conditions may result in soft tissue separating or tearing away from bone. When this occurs, surgery is required to mechanically reattach the soft tissue to bone to allow the soft tissue to naturally reattach itself to the bone. Surgical repair of soft tissue typically involves passing one or more strands of suture through the soft tissue, applying tension to the suture strands to draw the soft tissue into contact with the bone, and then securing the one or more suture strands ultimately to bone usually via one or more devices implanted in the bone to complete the repair.

A major source of failure of such surgical repairs occurs at the tissue-suture interface and is known as "suture pull-through." That is, one or more strands of suture may pull through the soft tissue. This can occur because a significant amount of tension is usually applied to the sutures to draw the soft tissue into contact with the bone, and because the individual suture strands, which are strong relative to the soft tissue, typically engage the tissue for only a short length. Suture pull-through is even more likely to occur when the suture strands run parallel to the soft tissue fibers. When pull-through occurs, the repair fails because the soft tissue is either no longer attached to the bone or not in sufficient contact with the bone to promote healing.

SUMMARY OF THE INVENTION

Soft tissue fixation according to the invention includes the passing of at least one suture through the tissue to be repaired. The passed suture is either preferably already in the form of a loop, or a loop is formed after the suture is passed through the soft tissue. The looped suture remains open and positioned on one side or surface of the soft tissue such that it is able to grab a large surface portion of the tissue in the loop. This improves the suture's grip on the tissue and decreases the likelihood that the suture will pull through the tissue, thus increasing the likelihood of surgical success.

In one embodiment of the invention, a suture is looped on itself yielding a looped end and at least one free end. The looped end is passed through a soft tissue to be repaired. The at least one free end is slidably connected through an anchoring structure. Such a structure may be a bone or suture anchor (referred to hereinafter as a suture anchor). The at least one free end is then passed through the soft tissue adjacent the looped end and then through the looped end, creating a grasping-type stitch, which also may be referred to as a cinch or loop-type stitch. Tension is applied to the at least one free end to pull the soft tissue into contact with the bone. The looped end remains open, grasping a large portion of the soft tissue surface opposite the bone. The at least one free end is then fastened ultimately to bone to maintain the tension, forming a looped suture construct that completes the repair.

In another embodiment of the invention, a suture anchor is pre-loaded with at least one looped suture, the looped suture having a looped end and one or two free ends. Pre-loaded suture anchors (i.e., suture anchors threaded with suture prior to implantation in bone) save the surgeon valuable time in the operating room. In those embodiments with one free end of suture, the original two free ends may be temporarily or permanently attached to each other to form the single free end, which in some instances may facilitate the surgical repair procedure. In other embodiments, one of the original two free ends may be tied off to the suture anchor, leaving one free end and one looped end for completing the looped suture construct. And in still other embodiments, the looped end may be formed by attaching one of the original free ends back on the suture itself and then slidably connecting the remaining free end through the suture anchor, leaving a looped end and a free end. Suture anchors of the invention may be pre-loaded with from one to six looped sutures.

BRIEF DESCRIPTION OF THE DRAWINGS

The above and other advantages of the invention will be apparent upon consideration of the following detailed description, taken in conjunction with the accompanying drawings, in which like reference characters refer to like parts throughout, and in which.

DETAILED DESCRIPTION OF THE INVENTION

The invention relates to apparatus and methods of fixing soft tissue to bone that improve the tissue-grasping strength of the suture and thus the likelihood of surgical success. In particular, by forming a looped suture construct in accordance with the invention, a larger surface area of soft tissue can be grabbed by the suture, which decreases the chance of suture pull-through.

Figure 1A:
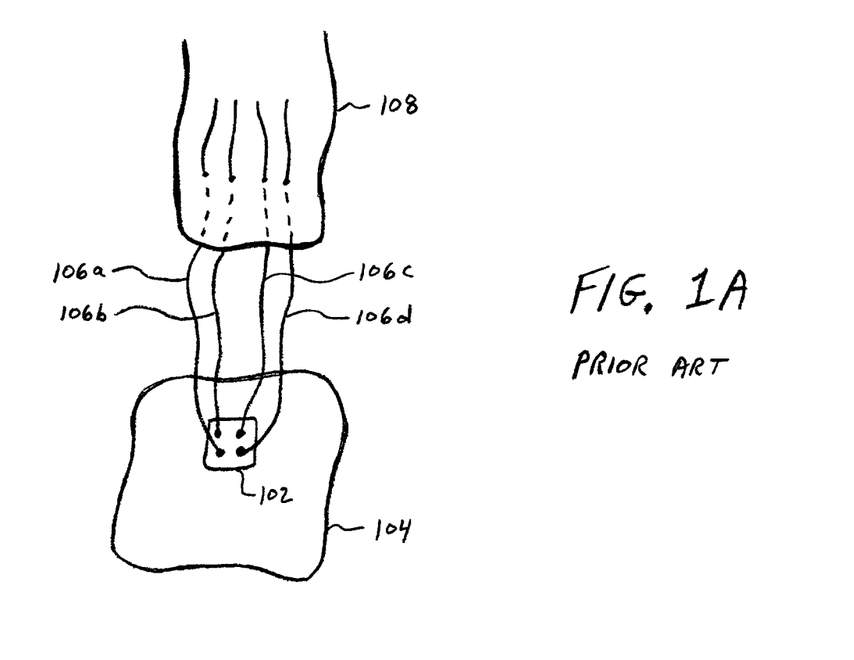
FIGS. 1A-1D are, respectively, top, corresponding front elevational, top, and corresponding front elevational views illustrating generally a known method of suturing soft tissue to bone.
Figure 1B:
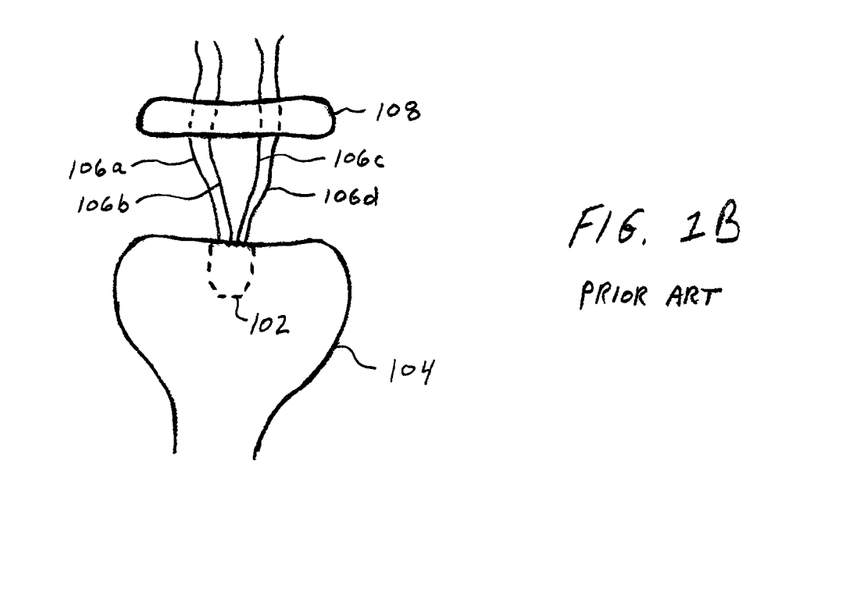

FIGS. 1A-1D illustrate generally a known method of repairing soft tissue torn or otherwise separated from bone. This method may be used in, for example, rotator cuff surgery, which may be open, mini-open, or arthroscopic. Such surgery typically involves selection of suture anchors, placement of those anchors, suture passage through the soft tissue, which in the case of rotator cuff repair is a tendon, and suture tying and/or other known suture fixation techniques. As shown in FIGS. 1A and 1B, a suture anchor 102 is implanted in a bone 104. Suture anchor 102 has suture strands 106*a-d* extending therefrom. Suture strands 106*a-d* may be four separate sutures each fixedly attached to anchor 102, or they may be a pair of sutures each slidably connected (via, e.g., an eyelet) through anchor 102. That is, suture strands 106*a* and 106*b* may be a single suture slidably connected through anchor 102, and suture strands 106*c* and 106*d* may be a second suture slidably connected through anchor 102. Alternatively, suture strands 106*a-d* may be three separate sutures, two fixedly attached to anchor 102 and the other slidably connected through anchor 102. Suture strands 106*a-d* may have been pre-loaded into anchor 102 before anchor 102 was implanted into bone 104, or a surgeon may attach suture strands 106*a-d* to implanted anchor 102 in situ.

Figure 1C:
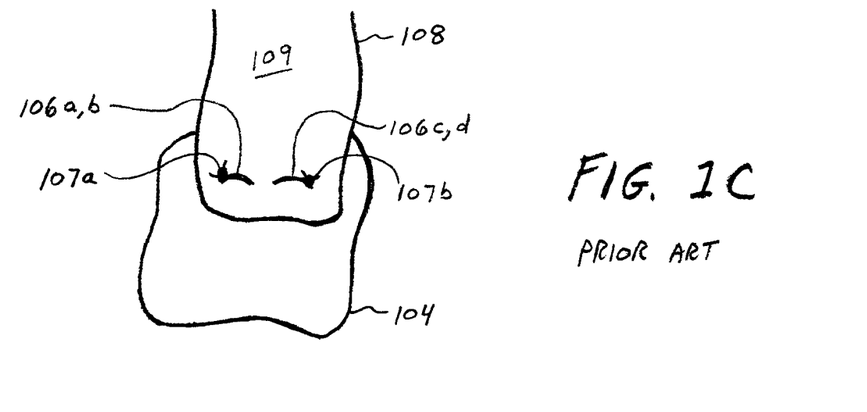
Figure 1D:
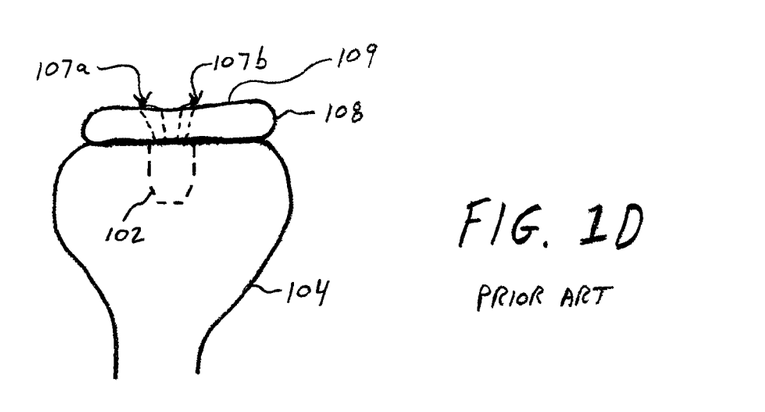

Suture strands 106*a-d* are each individually passed through tendon 108 with a specialized handheld surgical tool known variously as, for example, a sharp grasper, suture passer, tissue penetrator, passer instrument, or suture passing instrument. A wide variety of such specialized tools capable of passing suture through soft tissue are known, and each tool usually includes a handle, a tissue-grasping component (e.g., tongs), and a needle to pass the suture through the tissue. After suture strands 106*a-d* are passed through the soft tissue, tension is applied to the strands to pull tendon 108 into contact with bone 104, as shown in FIGS. 1C and 1D. Suture strands 106*a* and 106*b* and strands 106*c* and 106*d* may then be tied together, as illustrated by knots 107*a* and 107*b*, respectively, to mechanically hold tendon 108 in contact with bone 104, thus completing the repair. Note that the suture strands alternatively may be secured using knotless or other techniques known in the art.

One of the disadvantages of this suture construct is that one or both of suture sections 106*a,b* or 106*c,d* may pull through tendon 108 (particularly if they run parallel to the tendon fibers), because each section is likely under significant tension and each section engages topside tendon surface 109 for only a short length. An ideal rotator cuff repair should have a strong tissue grip that minimizes the formation of gaps between the tendon and bone and that maintains mechanical stability until healing occurs. Accordingly, even a partial suture pull-through may cause the repair to fail.

FIGS. 2A-2F illustrate an embodiment of the invention wherein soft tissue is surgically attached to bone using a looped suture construct. The looped suture constructs of the invention provide superior tissue-holding capabilities. Embodiment 200 preferably includes suture anchor 202, which is preferably pre-loaded with suture 206 having looped end 206*x* and free ends 206*y* and 206*z*. Suture 206 is made of one or more biocompatible fibers and may be, for example, #2 braided polyester. Suture 206 is slidably connected to anchor 202 such that the slidable connection is between looped end 206*x* and free ends 206*y* and 206*z*. The slidable connection allows suture 206 to slide smoothly through anchor 202 when pulled from preferably either the looped end side or the free ends side. Suture anchors having a slidable connection, which may be, for example, an eyelet, are known (other examples of slidable connections are described further below). Preferably pre-loaded, suture anchor 202 may then be implanted into bone 204. Suture anchor 202 may be of the type, for example, that is implanted by tapping the anchor into a pre-drilled or pre-punched hole in the bone or into bone directly (i.e., no pre-formed hole needed), resulting in a friction or press fit. Suture anchor 202 alternatively may be of another type of implantable suture anchor, examples of which are described further below. Looped end 206*x* and free ends 206*y* and 206*z* are now ready to be manipulated by the surgeon.

Figure 2A:
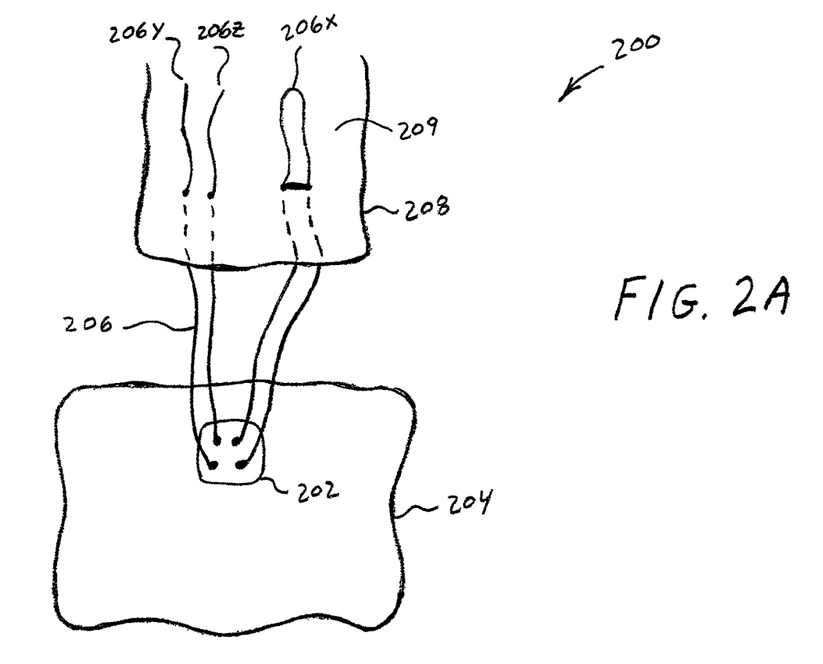
FIGS. 2A-2F illustrate an embodiment of the invention for suturing soft tissue to bone using a looped suture construct.
Figure 2B:
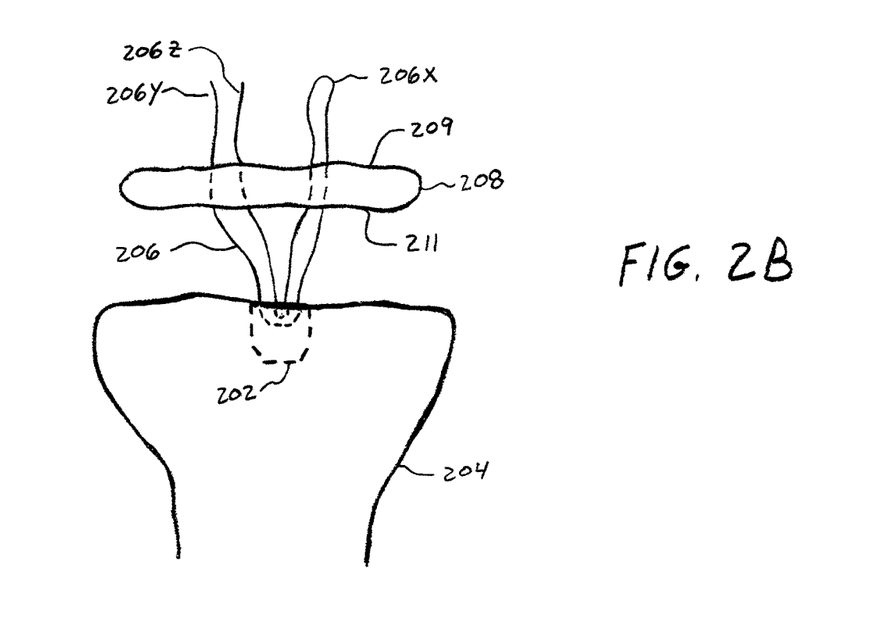

As shown in FIGS. 2A and 2B, looped end 206*x* is passed through tendon 208 from an underside surface 211 of the tendon (i.e., the surface facing bone 204) up through the opposite topside surface 209 of the tendon. Specialized surgical tools capable of passing a looped suture through soft tissue are known. Each of free ends 206*y* and 206*z* are also passed through tendon 208 from underside surface 211 and through topside surface 209 adjacent looped end 206*x*. For typical rotator cuff surgery, the distance between looped end 206*x* and free ends 206*y* and 206*z* may range from 2 mm to 15 mm. Note that each free end may be individually passed through tendon 208 or, alternatively, they may be passed together through tendon 208 with an appropriate surgical tool. Note also that while the terms "topside" and "underside" refer to the orientation of the surfaces as shown in the FIGS., they are not limited to any particular orientation (e.g., top, bottom, left, right). The "topside" surface refers to the surface of the soft tissue facing opposite or away from the bone, while the "underside" surface refers to the surface facing and ultimately coming into contact with the bone.

Figure 2C:
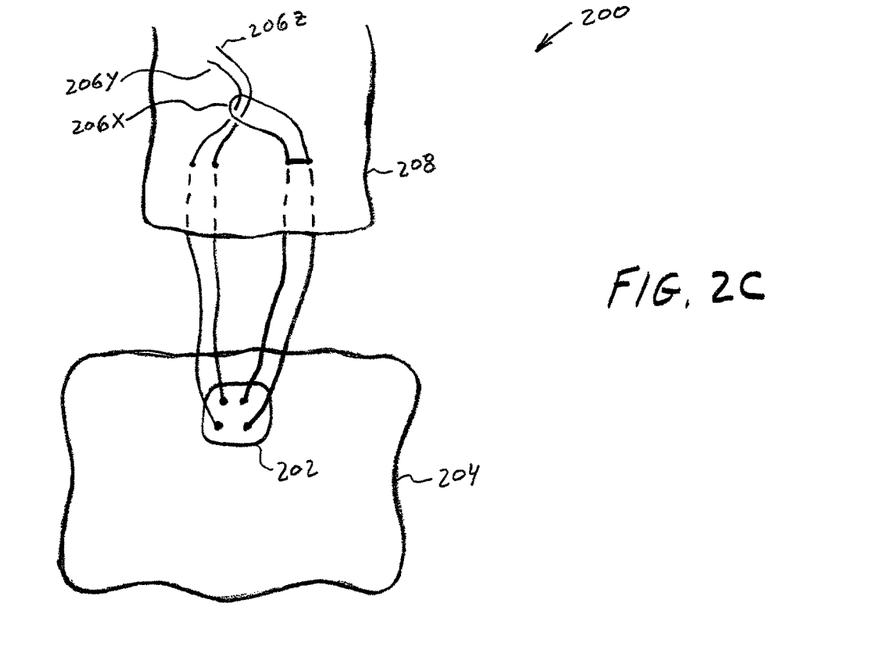
Figure 2D:
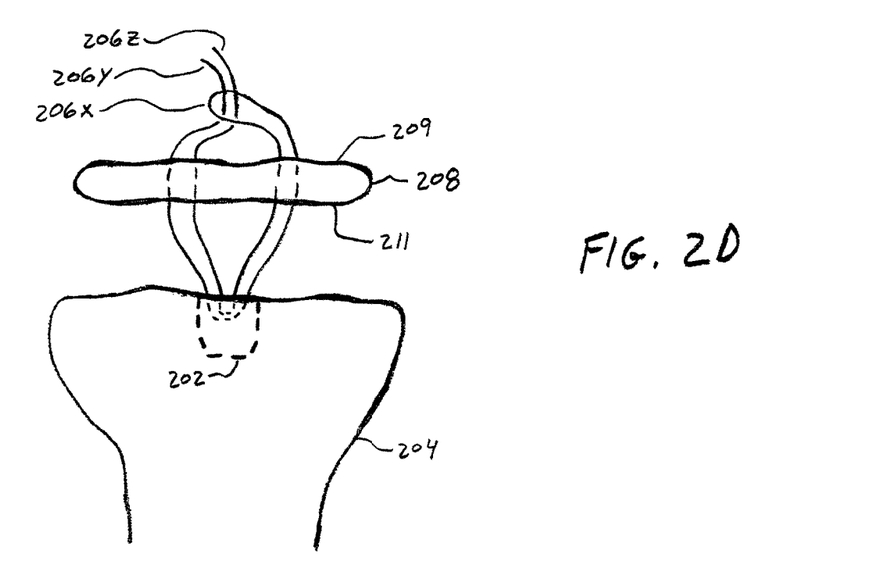
Figure 2E:
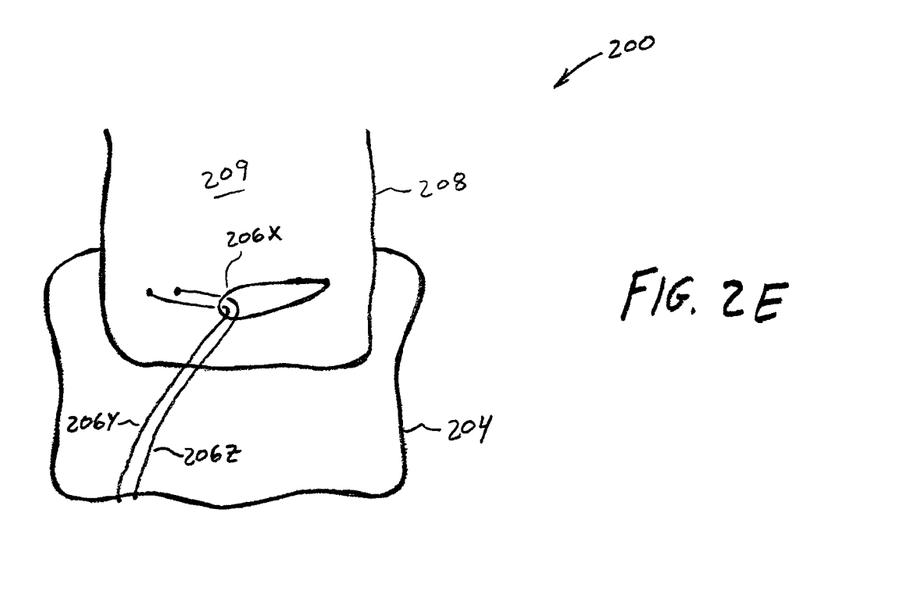
Figure 2F:
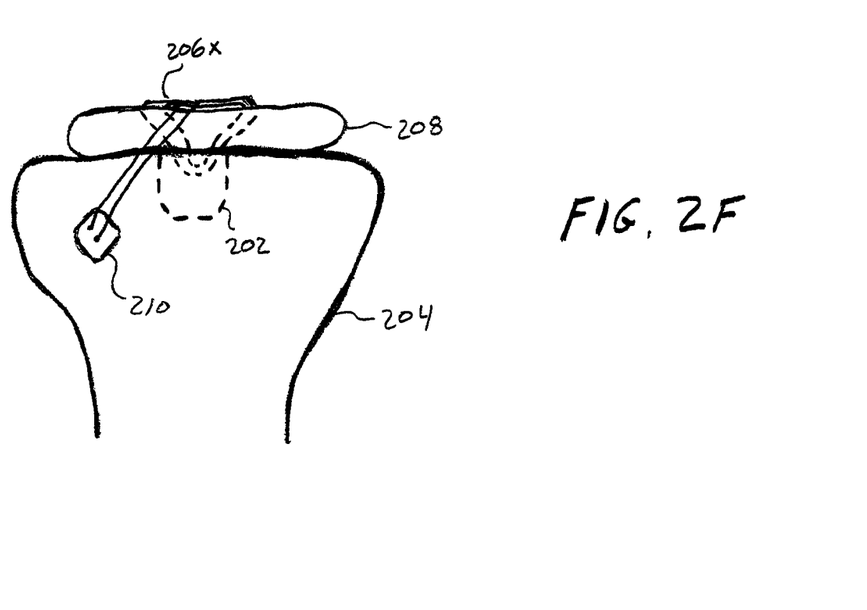

As shown in FIGS. 2C and 2D, free ends 206*y* and 206*z* are both passed through looped end 206*x*. Free ends 206*y* and 206*z* are then pulled tight (i.e., tension is applied) such that looped end 206*x* remains open and positioned on topside surface 209. That is, looped end 206*x* is not pulled tight into a knot, but remains open as shown in FIG. 2E. As free ends 206*y* and 206*z* are tightened, tendon 208 reduces to bone 204 (i.e., tendon 208 is pulled into contact with bone 204). Once tightened, free ends 206*y* and 206*z* may be fastened to one or more other suture anchors implanted in bone 204 (see, for example, suture anchor 210 in FIG. 2F) to complete the looped suture construct.

Figure 3A:
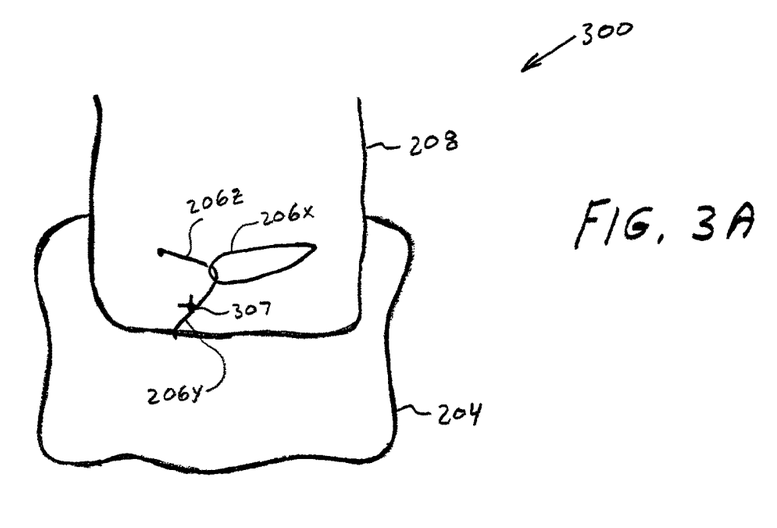
FIGS. 3A and 3B are top and corresponding front elevational views, respectively, illustrating an alternative embodiment of a looped suture construct according to the invention.
Figure 3B:
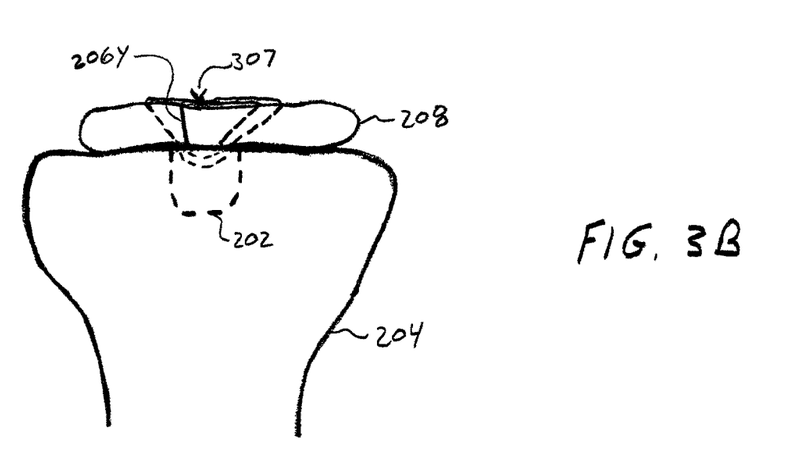
Figure 4:
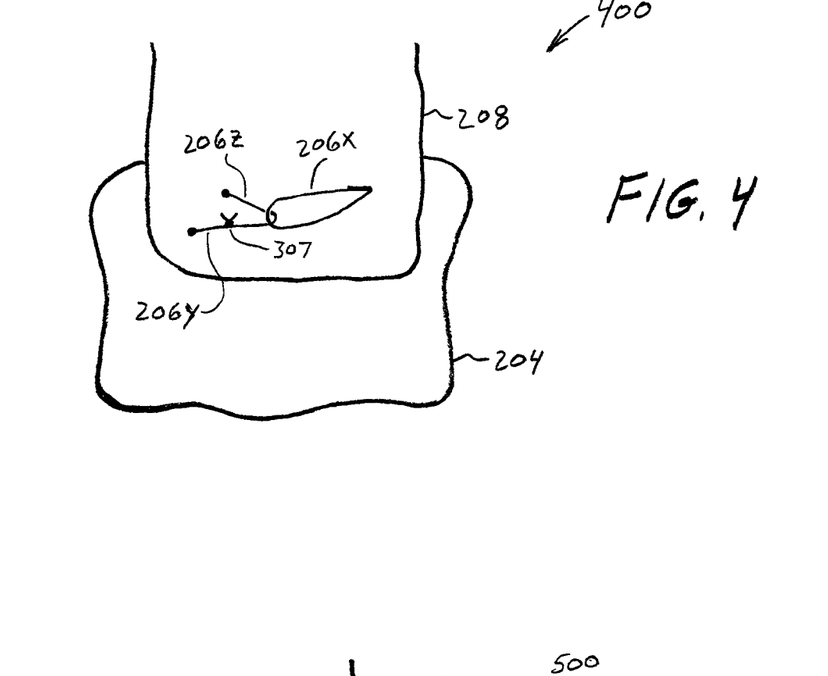
FIG. 4 illustrates another alternative embodiment of a looped suture construct according to the invention.

Note that other fastening techniques and configurations (including knotless fixation) of free ends 206*y* and 206*z* are possible. For example, in other embodiments of the invention, only one of free ends 206y and 206z is passed through tendon 208 and looped end 206x. The other free end may be tied off to the anchor or passed around the end of tendon 208 and fastened to the free end pulled tight through looped end 206x, as shown in FIGS. 3A and 3B. Alternatively, the other free end may also be passed through tendon 208, which may then be fastened to the free end pulled tight through looped end 206x, as shown in FIG. 4. The two free ends 206y and 206z may be fastened to each other by, for example, tying them into a knot 307 or by using a suitable adhesive or other fastening technique known in the art. Note also that each of free ends 206y and 206z may instead be fastened directly to bone, if feasible, or to another structure present at the surgical site. Such other structures may be another nearby bone or a previously implanted device that may be, for example, a bone clamp, plate, rod, pin or connecting device that may or may not be related to the soft tissue repair at hand. Such alternative constructs advantageously eliminate the need for second suture anchor 210, while still providing the same advantages as embodiment 200. Note further that suture anchor 202 also may not be needed if suitable bone and/or other structures are available at the surgical site to slidably connect and ultimately secure suture 206.

In another embodiment of the invention, suture 206 may not be pre-loaded into anchor 202. Instead, a surgeon may pass in situ a first free end of suture 206 through tendon 208 from underside surface 211 through topside surface 209, and then back through tendon 208 from topside surface 209 through underside surface 211, leaving a looped end on topside surface 209. The first free end, a second free end of suture 206, or both may then be slidably connected through suture anchor 202 or other suitable structure, whereupon one or both free ends may be passed back through tendon 208 from underside surface 211 through topside surface 209 adjacent the looped end. The two free ends may then be manipulated as described above.

Comparing the known suture construct of FIG. 1C with the looped suture constructs of FIGS. 2E, 3A, and 4 shows that suture 206 with its open loop positioned on topside surface 209 advantageously has a grasp on a larger surface portion of tendon 208 than does suture sections 106a,b and 106c,d combined. Moreover, the looped suture constructs of the invention advantageously have at least some portions of the looped suture that do not run parallel with fibers of the soft tissue. These advantages result in improved tissue-grasping strength while reducing the likelihood of suture pull-through.

Figure 5:
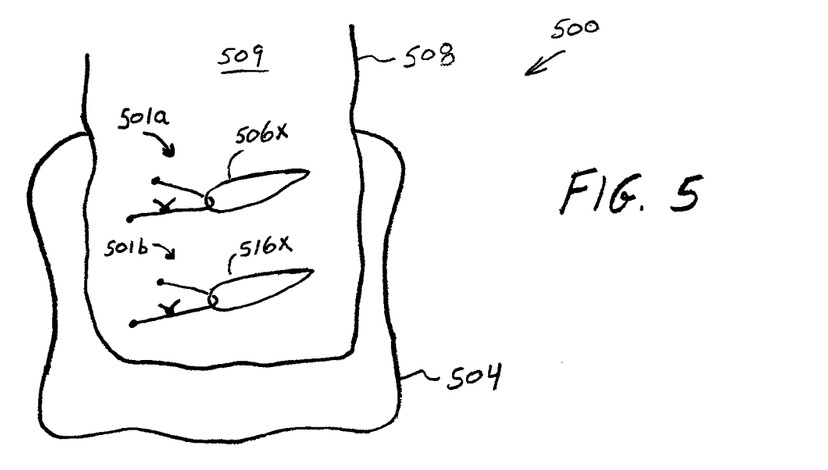
FIG. 5 illustrates an embodiment of the invention for suturing soft tissue to bone using a double-row looped suture construct according to the invention.

FIG. 5 shows an embodiment of the invention in which a double-row looped suture construct is used. In those surgical applications where, for example, a larger area of soft tissue 508 needs to be attached to bone 504, multiple looped suture constructs in accordance with the invention may be used. Note that although constructs 501a and 501b are shown as that of embodiment 400 (FIG. 4), other suture tying or fixation techniques, both as shown herein or as known in the art, may be used in each construct provided that looped ends 506x and 516x remain open and positioned on topside surface 509. For example, constructs 501a and 501b may each be that of any one of embodiments 200 (FIGS. 2E and 2F), 300 (FIGS. 3A and 3B), or 400 (FIG. 4).

Figure 6:
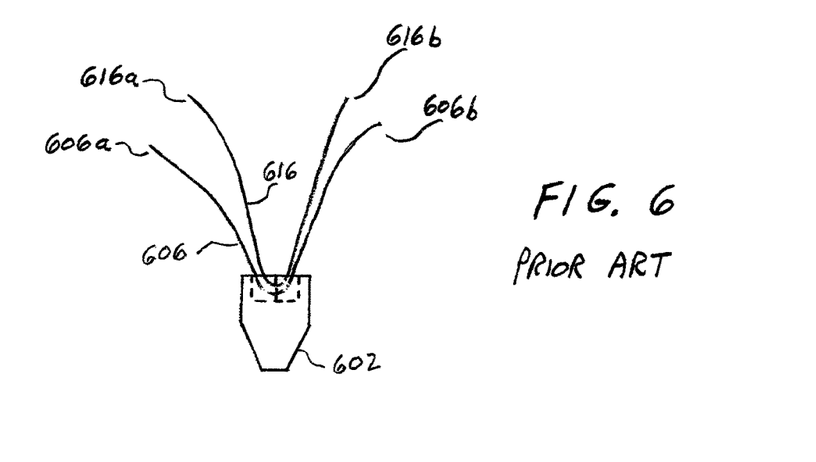
FIG. 6 illustrates generally a known suture anchor configuration wherein two sutures are each slidably connected through the anchor, leaving four free suture ends available for manipulation.

FIG. 6 shows a known suture anchor configuration wherein suture anchor 602 is pre-loaded with two sutures 606 and 616 each slidably connected to anchor 602. The slidable connection may be through an eyelet or equivalent structure in anchor 602, and allows either side of the suture to be pulled through the anchor. As shown, four free suture ends (i.e., suture ends 606a, 606b, 616a, and 616b) are available for manipulation by a surgeon. Known suture anchor 602 may be used, for example, in the known method of repairing soft tissue illustrated in FIGS. 1A-1D.

Figure 7:
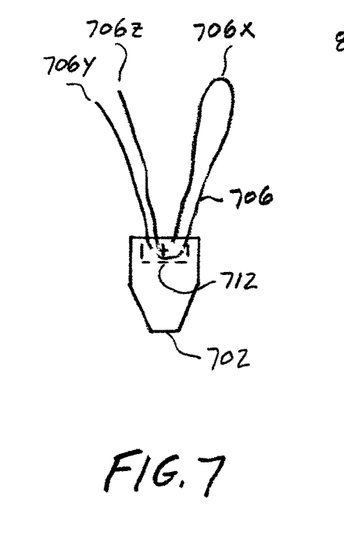
FIGS. 7-9 illustrate generally various embodiments of suture anchor configurations according to the invention wherein a long continuous suture is looped on itself and slidably connected through the anchor forming a looped end on one side of the slidable connection and one or two free ends on the other side of the slidable connection.
Figures 8, 9:
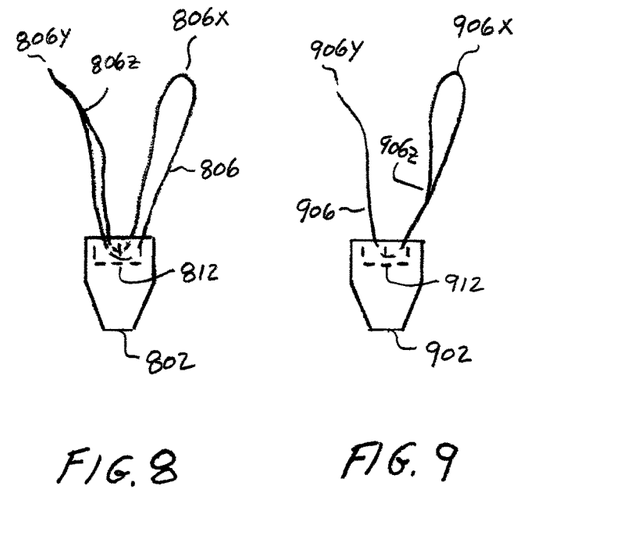

FIGS. 7-9 show several embodiments of suture anchor configurations according to the invention. In each configuration, a long continuous suture is slidably connected to the anchor such that a looped end extends from one side of the slidable connection, and one or two free ends of the suture extend from the other side of the slidable connection. The length of the suture depends on the surgical application. For example, in rotator cuff repair, the length of the suture may range from 10 cm to 100 cm. In FIG. 7, suture 706 forms a looped end 706x extending from one side of slidable connection 712 of suture anchor 702, while free ends 706y and 706z extend from the other side of slidable connection 712. FIG. 8 shows suture 806 slidably connected to suture anchor 802. Suture 806 has a looped end 806x extending from one side of slidable connection 812. The two ends of suture 806 extend from the other side of the slidable connection and are either temporarily or permanently bonded to each other to form a single free end 806y for easier passage through the soft tissue to be repaired in those surgical applications requiring such a suture free end configuration. The two ends 806y and 806z may be bonded to each other using any suitable technique known in the art. FIG. 9 shows suture anchor 902 pre-loaded with suture 906 having a looped end 906x formed on one side of slidable connection 912. As shown, suture end 906z is bonded back onto suture 906 on the same side of connection 912 as looped end 906x. The remaining free end 906y is threaded through slidable connection 912 and extends outward on the other side of connection 912. Suture end 906z may be bonded to suture 906 using any suitable technique known in the art. In those embodiments of the invention requiring a suture anchor, the suture anchor is preferably pre-loaded (i.e., prior to implantation) with at least one suture as shown in FIGS. 7-9.

Figure 10:
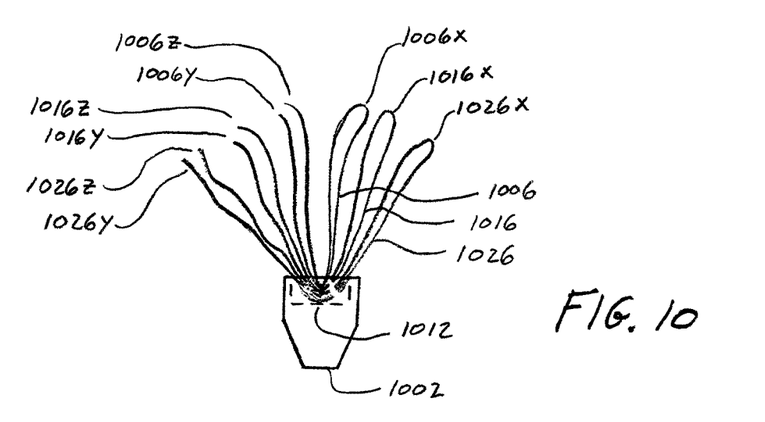
FIG. 10 illustrates generally an embodiment of a suture anchor configuration according to the invention wherein several long continuous sutures are slidably connected through the anchor, each suture forming a looped end on one side of the slidable connection and two free ends on the other side of the slidable connection.

FIG. 10 shows another embodiment of a suture anchor configuration according to the invention. Suture anchor 1002 is preferably pre-loaded with three sutures 1006, 1016, and 1026. Each suture has a looped end (i.e., 1006x, 1016x, and 1026x) extending from one side of slidable connection 1012 and, in this embodiment, two free ends (i.e., 1006y and 1006z, 1016y and 1016z, and 1026y and 1026z) extending from the other side of slidable connection 1012. Suture anchors configured in accordance with the invention may have from one to six sutures pre-loaded therein. The pre-loaded sutures may be in any one of the looped forms shown in FIGS. 7-9, and may be in any combination of the looped forms shown in FIGS. 7-9. One or more of the sutures optionally may be a different color (e.g., blue, green, white, etc.).

Suture anchors have a generally cylindrical body that may be tapered and have one or more surface features for engaging bone or another implanted device, depending on the manner in which the suture anchor is to be implanted into bone. For example, suture anchors may be screwed, twisted, friction or press-fitted, punched, or otherwise fastened to the bone. Suture anchors can be of various lengths and may range in diameter from 1 mm to 15 mm.

Figure 11:
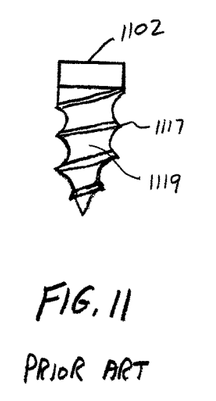
FIGS. 11-13 illustrate generally various embodiments of suture anchor body configurations that can be used with the invention.
Figure 12:
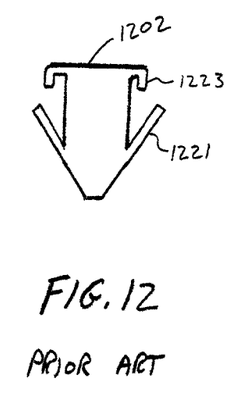
Figure 13:
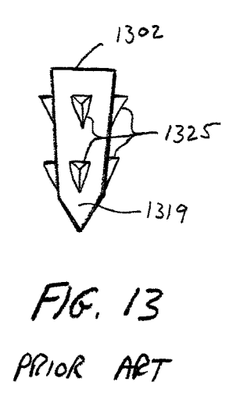

FIGS. 11-13 illustrate generally some of the known suture anchor body type configurations that can be used in accordance with the invention. FIG. 11 shows a threaded suture anchor 1102 having a continuous helical thread 1117 wrapping around body 1119, which tapers to a narrow point. As is known, the height and pitch of the thread can vary. Thread 1117 may be a self-tapping thread that allows anchor 1102 to be screwed directly into bone without first having to drill a pilot hole. Alternatively, thread 1117 may be conventional requiring a pre-drilled hole in the bone. FIG. 12 shows a tap-in type suture anchor 1202 that can either be tapped directly into bone or into a pre-drilled hole in the bone or a hollow anchoring sleeve pre-installed in the bone. Suture anchor 1202 preferably has a plurality of prongs 1221 that engage the bone or anchoring sleeve to securely hold the anchor in place (see, e.g., U.S. Pat. No. 6,143,017). Suture anchor 1202 may also have, for example, a plurality of suture engaging hooks 1223 for slidably connecting one or more sutures thereto. Note that hooks 1223 may also be included in other embodiments of suture anchors. FIG. 13 shows a wedge-like suture anchor 1302 having a plurality of teeth for engaging bone (see, e.g., U.S. Pat. No. 7,217,279). Bone teeth 1325 are oriented longitudinally to facilitate insertion (either directly into bone or into a pilot hole in the bone) and retention of the anchor thereafter, and may vary in number, size, and location on body 1319. Although the shape of teeth 1325 is shown as basically triangular or pyramidal, other shapes are possible. Note that the embodiments of the invention requiring one or more suture anchors are not limited to the body types shown in FIGS. 11-13.

Suture anchors also have a suture attaching mechanism. Such mechanisms are known and can vary widely as to configuration and features for connecting and securing suture to the anchor. A suture attaching mechanism may be made up of one or more separate parts assembled together and attached to the body of the anchor, or it may be formed integrally with the anchor body. For use in accordance with the invention, a suture attaching mechanism should at least initially provide a slidable connection for one or more sutures attached thereto. That is, a suture connected to the suture attaching mechanism should be able to be pulled easily through the suture anchor from at least one side of the suture attaching mechanism at least initially. For example, some known suture anchors may have an internal locking device that initially allows the suture to slide through the attaching mechanism and thereafter allows a surgeon to lock the suture in place. Another known anchor allows the suture to slide through when pulled in one direction and locks the suture in place when the suture is pulled in the opposite direction.

Figure 14:
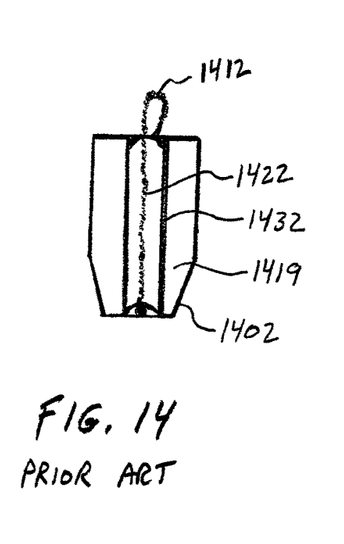
FIGS. 14-16 illustrate generally various embodiments of suture anchor slidable-connection configurations that can be used with the invention.
Figure 15:
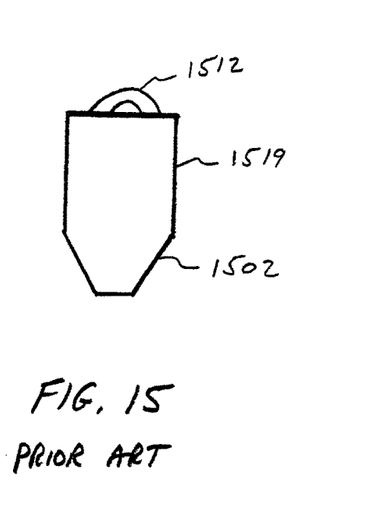
Figure 16:
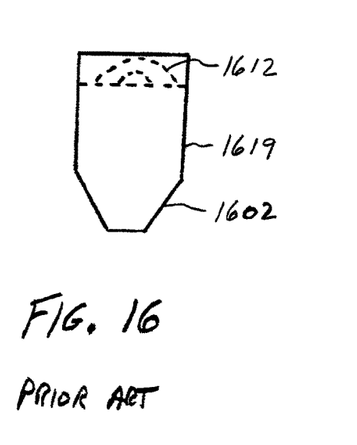

FIGS. 14-17 show various embodiments of suture anchors having suture attaching mechanisms that can be used with the invention. FIG. 14 shows an embodiment of a suture anchor 1402 having an eyelet 1412 formed by a suture loop or biocompatible wire 1422 that extends longitudinally around suture anchor body 1419 in longitudinal channel 1432 (see again, e.g., U.S. Pat. No. 7,217,279). In other similar embodiments, the loop of suture or wire is disposed/secured within the body of the anchor, sometimes with a separate, insertable part. FIG. 15 shows suture anchor 1502 having a suture attaching mechanism in the form of an eyelet 1512 integrally extending from a top surface of anchor body 1519, while FIG. 16 shows suture anchor 1602 having a recessed eyelet 1612 within a top portion of anchor body 1619. Recessed eyelet 1602 is preferably flush with a top surface of anchor 1602 (i.e., the eyelet does not project beyond or outside the top surface).

Figure 17:
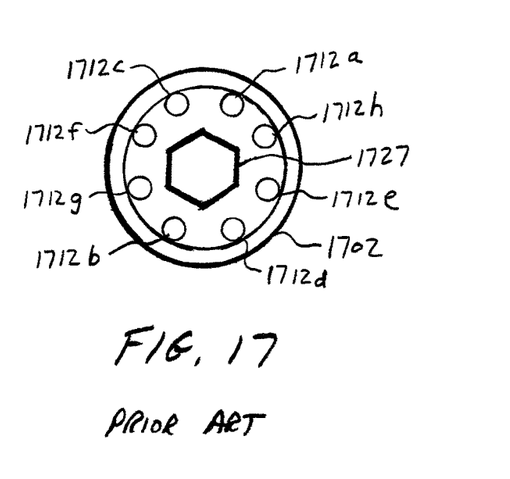
FIG. 17 is a top view illustrating another embodiment of a suture anchor configuration that can be used with the invention.

FIG. 17 is a top view of another embodiment of a suture anchor that can be used with the invention. Suture anchor 1702 has a plurality of suture ports 1712*a-h* spaced apart around the circumference of the anchor head. Pairs of suture ports may be connected together via internal U-shaped channels or passageways (not shown) within the body of the anchor to provide sutures with a slidable connection to anchor 1702. For example, suture ports 1712*a* and 1712*b* may be connected together internally such that a suture threaded into port 1712*a* exits from port 1712*b* (and vice versa). Similarly, suture ports 1712*c* and 1712*d*, 1712*e* and 1712*f*, and 1712*g* and 1712*h* may also be connected together internally to provide a slidable connection to sutures respectively threaded there through. In the embodiment shown, four sutures configured in accordance with the invention (i.e., each looped on itself) may be pre-loaded into anchor 1702. Suture anchor 1702 also has a drive socket 1727 configured to be engaged by a complementary drive tool capable of driving the suture anchor into bone via screwing, twisting, tapping, or otherwise installing the anchor into bone, depending on the type of anchor body and surface features. Note that the drive socket and complementary tool are not limited to the hexagonal shape shown, but may be of other suitable geometries. Note that those embodiments of the invention requiring one or more suture anchors are not limited to the suture attaching mechanisms shown in FIGS. 14-17.

Suture anchors of the invention may be made of one or more biocompatible materials and/or composites thereof as is known in the art. Such materials may include various non-absorbable materials such as metals and metal alloys including, but not limited to, stainless steel, titanium, Nitanol, cobalt, and non-absorbable polyesters. Suture anchor materials may also include various bioabsorbable plastics and other materials including, but not limited to, polyglycolic or polylactic acid polymers. Furthermore, still other materials, such as carbon fiber and other suitable polymers, may be used. Suture anchors of the invention may be made as a single unit using conventional shaping or molding techniques, or they may be made in separate parts assembled together also using conventional methods and techniques.

Note that the invention is not limited to only those suture anchors shown in the FIGS. Various other types of suture anchor configurations, including those configured with any suitable combination of features disclosed herein as well as others known in the art, may be used in accordance with the invention, provided that they include a slidable suture connection operative to receive at least one suture having a looped end and one or two free ends as described above.

In addition to rotator cuff surgery, the looped suture constructs and pre-loaded suture anchors of the invention may be used in a variety of other medical procedures throughout different areas of the body. For example, the invention may be used in biceps tenodesis (proximal or distal), labral and other soft tissue repairs in the shoulder and hip joints, ACL (anterior cruciate ligament) procedures, ligament repairs and reconstruction in the upper and lower extremities, and ligament repairs and reconstruction in the hand/wrist and elbow. The looped suture constructs of the invention advantageously can be of different sizes to accommodate different sized soft tissue fixation.

While a preferred embodiment of the invention has been described and disclosed, modifications to the methods and apparatus described herein are still possible within the scope of the invention. For example, although reference has been made throughout this disclosure to the attachment of suture anchors and suture constructs to bone, the suture anchors and constructs described herein are not limited to attachment to only bone. Alternatively, they may be attached to other structures, such as, for example, suitable implanted devices or constructs. Such implanted devices and constructs may include, for example, hip and knee replacement parts and various types of bone clamps, plates, rods, pins, and related connecting devices.

Note that some embodiments of the invention may not require a suture anchor. For example, a looped suture construct in accordance with the invention may be anchored directly to bone at a surgical site where the bone has features that allow one or more suture free ends to be slidably connected thereto and ultimately secured. The bone features may be natural or surgeon created (e.g., a drilled through-hole through a section of bone to slidably connect a suture). Accordingly, the term "suture attaching mechanism" as used herein is not necessarily limited to a mechanical device, but may also refer to a suitable bone feature that can be used as such.

Note also that the methods and apparatus disclosed herein are not limited to the medical treatment of humans but, alternatively, may be applied to the treatment of animals or used in various educational and/or research activities. For example, the methods and apparatus may be used on cadavers, nonliving animal parts, and/or synthetic parts (that, e.g., simulate soft tissue and bone) for teaching purposes and/or laboratory studies.

Thus it is seen that apparatus and methods of soft tissue fixation using a looped suture construct and, where needed, pre-loaded suture anchors are provided. One skilled in the art will appreciate that the invention can be practiced by other than the described embodiments, which are presented for purposes of illustration and not of limitation, and the invention is limited only by the following claims.

I claim:

1. A method of suturing soft tissue comprising:
passing a loop of suture through soft tissue, the loop of suture exiting the tissue through a first location on a tissue surface;
passing a first free end of the suture through the soft tissue adjacent the loop of suture, the first free end of the suture exiting the tissue through a second location on the tissue surface, wherein the suture is slidably connected to a suture attaching mechanism of an anchoring structure such that the attaching mechanism is between the loop of suture and the first free end of the suture;
passing a second free end of the suture through the soft tissue adjacent the loop of suture, the second free end of suture exiting the tissue through a third location on the tissue surface, wherein the suture attaching mechanism is between the loop of suture and the second free end of the suture;
passing the first free end of the suture through the loop of suture;
applying tension to the first free end of the suture such that the soft tissue is pulled into contact with a desired structure and the loop of suture remains open and positioned on the first tissue surface, wherein the desired structure is bone, the anchoring structure or a second anchoring structure; and
securing the first free end of the suture to maintain the applied tension.

2. The method of claim 1 further comprising prior to the passing of the first free end of suture through the soft tissue:
passing the first free end of the suture through the suture attaching mechanism of the anchoring structure.

3. The method of claim 1 further comprising:
passing the second free end of the suture through the loop of suture;
applying tension to the second free end of the suture such that the soft tissue is pulled into contact with the desired structure and the loop of suture remains open and positioned on the first tissue surface; and
securing the second free end of the suture to maintain the applied tension on the second free end.

4. The method of claim 1 wherein the securing of the first free end of the suture to maintain the applied tension comprises:
securing the second free end of the suture to the first free end of the suture to maintain the applied tension.

5. The method of claim 1 wherein the securing of the first free end of the suture to maintain the applied tension comprises attaching the first free end of the suture to a suture anchor implanted in the desired structure.

6. The method of claim 1 further comprising implanting the anchoring structure into bone.

7. The method of claim 1 wherein the anchoring structure has the loop of suture and the first free end of the suture pre-loaded therein such that the suture attaching mechanism is between the loop of suture and the first free end of the suture.

8. The method of claim 1 wherein the anchoring structure comprises a suture anchor.

9. The method of claim 1 wherein the suture attaching mechanism comprises an eyelet.

10. The method of claim 1 wherein the desired structure comprises bone.

11. The method of claim 1 wherein the anchoring structure and the desired structure are the same.

12. The method of claim 1 wherein the soft tissue comprises a tendon, ligament, or muscle.

13. The method of claim 1 further comprising:
securing the second free end of the suture to maintain the applied tension on the second free end.

14. The method of claim 13 wherein the securing of the second free end of the suture to maintain the applied tension comprises:
attaching the second free end of the suture to the anchoring structure.

15. The method of claim 13 wherein the securing of the second free end of the suture to maintain the applied tension comprises:
attaching the second free end of the suture to the first free end of the suture.

16. A method of suturing soft tissue comprising:
passing a first free end of suture through soft tissue, the first free end exiting the tissue through a first tissue surface;
passing the first free end of suture back through the soft tissue to form a loop of suture on the first tissue surface, the first free end exiting the tissue through a second tissue surface;
passing a second free end of the suture through the soft tissue adjacent the loop of suture, the second free end exiting the tissue through the first tissue surface, wherein the
suture is slidably connected to a suture attaching mechanism of an anchoring structure such that the attaching mechanism is between the loop of suture and the second free end;
passing the second free end of the suture through the loop of suture;
applying tension to the first and second free ends of the suture such that the soft tissue is pulled into contact with a desired structure and the loop of suture remains open and positioned on the first tissue surface, wherein the desired structure is bone or the anchoring structure; and
securing the first and second free ends of the suture to maintain the applied tension.

17. A method of suturing soft tissue comprising:
passing a first free end of suture through soft tissue, the first free end exiting the tissue through a first tissue surface;
passing the first free end of suture back through the soft tissue to form a loop of suture on the first tissue surface, the first free end exiting the tissue through a second tissue surface;
passing a second free end of the suture through the soft tissue adjacent the loop of suture, the second free end exiting the tissue through the first tissue surface, wherein the
suture is slidably connected to a suture attaching mechanism of an anchoring structure such that the attaching mechanism is between the loop of suture and the second free end;
passing the first free end of the suture through the loop of suture;
applying tension to the first and second free ends of the suture such that the soft tissue is pulled into contact with a desired structure and the loop of suture remains open and positioned on the first tissue surface, wherein the desired structure is bone or the anchoring structure; and securing the first and second free ends of the suture to maintain the applied tension.

18. The method of claim 16 or claim 17 further comprising passing the first free end of the suture through the suture attaching mechanism of the anchoring structure after forming the loop of suture.

19. The method of claim 18 wherein the securing of the first and second free ends comprises:
passing the first free end of suture through the soft tissue after passing the first free end through the suture attaching mechanism, the first free end exiting the tissue through the first tissue surface; and
tying the first and second free ends of the suture together into a knot.

20. The method of claim 16 or claim 17 further comprising pre-loading the anchoring structure with the suture such that the suture attaching mechanism is between the first and second free ends of the suture.

21. The method of claim 20 further comprising implanting the anchoring structure into bone.

* * * * *